US010278679B2

(12) United States Patent
Melendez et al.

(10) Patent No.: US 10,278,679 B2
(45) Date of Patent: May 7, 2019

(54) VAGINAL CELL OR CERVICAL CELL COLLECTION DEVICE

(71) Applicant: MEL-MONT MEDICAL, LLC, Miami, FL (US)

(72) Inventors: Frank Melendez, Miami, FL (US); Liliana Montes, Cali (CO)

(73) Assignee: MEL-MONT MEDICAL, LLC

( * ) Notice: Subject to any disclaimer, the term of this patent is extended or adjusted under 35 U.S.C. 154(b) by 268 days.

(21) Appl. No.: 15/204,007

(22) Filed: Jul. 7, 2016

(65) Prior Publication Data
US 2018/0008245 A1    Jan. 11, 2018

(51) Int. Cl.
   *G01N 1/02*    (2006.01)
   *A61B 10/02*    (2006.01)
   *A61B 17/00*    (2006.01)

(52) U.S. Cl.
   CPC .......... *A61B 10/0291* (2013.01); *A61B 10/02* (2013.01); *A61B 2010/0216* (2013.01); *A61B 2017/00951* (2013.01); *G01N 2001/028* (2013.01)

(58) Field of Classification Search
   CPC ................ A61B 10/02; A61B 10/0291; A61B 2010/0216; A61B 2017/00951; G01N 2001/028
   See application file for complete search history.

(56) References Cited

U.S. PATENT DOCUMENTS

| | | | | |
|---|---|---|---|---|
| 3,633,565 A | * | 1/1972 | McDonald | A61B 10/0291 600/570 |
| 3,838,681 A | * | 10/1974 | Dalton | A61B 10/04 600/570 |
| 4,027,658 A | * | 6/1977 | Marshall | A61B 10/02 600/570 |
| 4,951,684 A | * | 8/1990 | McMillan | A61B 10/02 600/571 |
| 4,981,143 A | * | 1/1991 | Sakita | A61B 10/0291 600/570 |
| 5,137,030 A | * | 8/1992 | Darougar | A61B 10/02 600/570 |
| 6,346,086 B1 | * | 2/2002 | Maksem | A61B 10/0291 600/569 |
| 7,749,173 B2 | * | 7/2010 | Larkin | A61B 10/02 600/562 |

(Continued)

*Primary Examiner* — Sean P Dougherty

(57) ABSTRACT

A self-sampling device used for collecting a homogenized sample of cells from different areas within the vaginal canal by a user. The device, comprises a hollow, cylindrical elongated tubing, a cell collecting area which is covered by an adhesive collecting element is disposed at one end, a channel disposed along the length of the cell collecting area for collecting the cells from different areas along length of the vaginal canal via one insertion, so as to mix the cells within the channel resulting in the homogenized collection of cells, further the collecting element has plurality of organized ridges arranged along the length of the cell collecting area to facilitate cell collection and a handle comprising an ergonomically shaped finger grip, wherein one end of the finger grip having a design or marking to facilitate easy counting of the complete rotations of the device, the handle and the tubing is designed to form a unitary structure.

14 Claims, 4 Drawing Sheets

(56) References Cited

U.S. PATENT DOCUMENTS

| | | | | |
|---|---|---|---|---|
| 8,439,847 B2* | 5/2013 | Larkin | A61B 10/02 600/562 |
| 8,551,016 B2* | 10/2013 | Slowey | A61B 10/0045 600/573 |
| 8,641,642 B2* | 2/2014 | Giddings | A61B 10/0051 600/570 |
| 9,060,753 B2* | 6/2015 | Lundkvist | A61B 10/0096 |
| 9,382,577 B2* | 7/2016 | Ogden | G01N 1/02 |
| 2004/0030263 A1* | 2/2004 | Dubrul | A61B 10/02 600/565 |
| 2004/0153000 A1* | 8/2004 | Pevoto | A61B 10/0045 600/562 |
| 2008/0294183 A1* | 11/2008 | O | A61M 25/0637 606/185 |
| 2011/0213270 A1* | 9/2011 | Pison | A61B 10/02 600/562 |
| 2011/0262951 A1* | 10/2011 | Young | A61B 10/0045 435/29 |
| 2014/0249450 A1* | 9/2014 | Klein | A61B 10/0291 600/569 |
| 2016/0331357 A1* | 11/2016 | Czarnecki | A61B 10/02 |
| 2016/0367227 A1* | 12/2016 | Triva | A61B 10/0045 |
| 2018/0008245 A1* | 1/2018 | Melendez | A61B 10/0291 |

\* cited by examiner

VAGINAL CELL OR CERVICAL CELL COLLECTION DEVICE

FIELD OF THE INVENTION

The present invention relates generally to a vaginal cells or cervical cell collection device and more particularly it relates to a vaginal or cervical homogenized cell self-sampling device.

BACKGROUND OF THE INVENTION

The collection of cell samples for cervical cytology and Human Papilloma Virus (HPV) testing is critical in organized screening cervical cancer prevention efforts. Therefore, the need for better sample taking techniques and improved medical devices (cervical-vaginal sampling device) is a must in public and private health screening programs. The reason why the development of a self-collected sample technique is imperative, because in traditional settings, cells are obtained during speculum examination, however, not all women welcome pelvic examination done by a healthcare provider.

Numerous innovations have been provided in prior art that are adapted to a variety of self-sampling devices available for samplings that easily are adaptable to existing screening programs. Even though these innovations may be suitable for the specific purposes to which they address, however, they would not be as suitable for the purposes of the present invention.

U.S. patent application. No. 20,150,297,196 to Ching et al. discloses about a device and a method for collection of a biological sample during insertion into a human orifice. The device may include a body piece, an insertion piece extending from one end of the body piece, and a handle connected to the other end of the body piece. The collection end may be a swab with a plurality of pin wheeling fins having leading edge oriented to collect the biological sample when the shaft is rotated in a given direction. However it limits the ability to collect enough quality and quantity of cellular material as well as the handle is having no provision for keeping track of the number of rotations of the device by the patient herself.

U.S. patent application. No. 20,150,230,872 to Lundkvist et al, discloses about a sampling system for an individual to self-collect sample form mucous tissue. The collecting device has a flexible shaft having a handle at one end and a sample collecting element removably connectable with the other end of the shaft and operable to collect a cell sample from mucous tissue of an individual. However the collecting device is too short, thus has limited ability to collect specimens from different areas of the female reproductive track in a single insertion. Further the semi-flat surface of the device reduces the ability to collect enough quantity and quality of cellular material to perform multiple tests at one single sampling. Further the handle is too thin to hold and rotate, thereby increasing the risk of over introduced the device into the vagina and additionally, it is difficult to rotate the device once introduced into the vaginal canal and hard to keep track of the number of 360 degrees rotations by the patient herself.

It is apparent now that numerous innovations for a variety of self-sampling devices have been developed in the prior art that are adequate for various purposes. Furthermore, even though these innovations may be suitable for the specific purposes to which they address, accordingly, they would not be suitable for the purposes of the present invention as heretofore described. Thus there is a need for an improved self-sampling device is needed.

SUMMARY OF THE INVENTION

The present invention discloses about a vaginal or cervical homogenized cell self-sampling device. With the above-noted prior art and inadequacies in mind, it is an object of the present invention to provide an improved self-sampling device which is capable of collecting enough quality and quantity of cells from different areas of the long vaginal canal is needed, wherein the cells are collected all the way from the major labia going through the vulva to the external surface of the cervix (ectocervix) and the cervical canal (endocervix) including the transformation zone (squamocu-lumnar junction) are needed to be obtained for reliable testing results. The reasons behind this theory is the result of the exponential increase of vulvar and vaginal cancer cases in addition to cervical cancer in women who do not participate in conventional screening programs, but rather use a traditional self-collecting device to obtain samples for HPV testing, which does not yield in collecting enough quality and quantity of homogenized vaginal cells or cervical cells.

In view of the foregoing, it is therefore another object of the present invention to provide a specially designed finger grip of the device to keep track of the number of 360 degrees rotations by the patient herself.

It is still another object of the present invention to provide a channel along the cell collecting area of the device, wherein the channel acts as a means for collecting a homogenized sample of cells from different areas within the vaginal canal via one insertion/collection.

It is further another object of the present invention to provide a grip which is inexpensive to manufacture, easy and quick to use and collect enough homogenized vaginal cells or cervical cells by the user herself.

In accordance with one aspect of the present invention, a device for collecting a homogenized sample of cells from different areas within the vaginal canal by a user, wherein the device, comprising, a hollow, cylindrical elongated tubing having a distal end and a proximal end; a cell collecting area disposed at the distal end of the elongated tubing, wherein the cell collecting area is covered by an adhesive collecting element extending to a predetermined distance from the edge of the distal end, further the collecting element has plurality of organized ridges arranged in several parallel rows along the length of the cell collecting area; a channel, wherein the channel is disposed along the length of the cell collecting area for collecting the cells from different areas along length of the vaginal canal via one insertion, so as to mix the cells within the channel resulting in the homogenized collection of cells; and a handle, wherein the handle is disposed at the proximal end of the tubing, further the handle comprises an ergonomically shaped finger grip, wherein one end of the finger grip having a design or marking, the handle and the tubing is designed to form a unitary structure.

In another aspect of the invention, a method for collecting vaginal cells or cervical cells by a user, wherein the method, comprising the steps of, holding a handle of a self-sampling device, wherein the device comprising a hollow, cylindrical elongated tubing having a distal end and a proximal end, wherein the handle is disposed at the proximal end of the tubing and is attached to the base of the device and a cell collecting area disposed at the distal end of the elongated tubing; inserting the device into the vaginal canal; rotating the device by the patient herself for at least three number of 360 degrees rotations to secure proper cell collection, wherein the handle comprises a butterfly shaped finger grip having both sides of one end of the finger grip is texture designed to facilitate counting predetermined number of 360 degrees rotations of the device, further the butterfly shaped finger grip, the handle and the tubing is one piece to prevent the device to be introduced more than necessary to collect the cells; and collecting the cells by a cell collecting area having a channel disposed along the length of the cell collecting area for accumulating homogenized sample of cells from different areas within the vaginal canal via one insertion, wherein the cell collecting area is covered by an adhesive collecting element that is 3.5 to 4.5 centimeters long and 0.5 to 0.9 millimeters in diameter, further the collecting element has organized ridges throughout the surface to improve cellular material retaining properties of the collecting element.

In another aspect of the invention, the collecting area elongating from approximately 0.3 millimeters below the edge of the distal end of the tubing to approximately 0.3 millimeters before the bottom part of the collecting element.

In another aspect of the invention, the channel is 0.3 millimeters in depth and 0.3 millimeters wide.

In another aspect of the invention, the ridges are arranged in organized fashion in at least six rows and at least seventeen ridges per row throughout the cell collecting area.

Other features and aspects of the invention will become apparent from the following detailed description, taken in conjunction with the accompanying drawings, which illustrate, by way of example, the features in accordance with embodiments of the invention. The summary is not intended to limit the scope of the invention, which is defined solely by the claims attached hereto.

BRIEF DESCRIPTION OF THE DRAWINGS

The invention will now be described, by way of example, with reference to the accompanying drawings, in which.

Like reference numerals refer to like parts throughout the various views of the drawings.

DETAILED DESCRIPTION OF THE INVENTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper," "lower," "left," "rearward," "right," "forward," "vertical," "horizontal," and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Specific dimensions and other physical characteristics relating to the embodiments disclosed herein are therefore not to be considered as limiting, unless the claims expressly state otherwise.

A vaginal or cervical cell collection device 100 acting as a self-sampling device having a specially designed finger grip 118 and a channel 114 to accumulate homogenized cell is referenced in FIGS. 1-5. In some embodiments, the present invention teaches the channel 114, which acts as a means for collecting a homogenized sample of cells from different areas within the vaginal canal via one insertion or collection. The channel 114 runs the length of the collecting tool 108, and can capture cells along the length of the canal, where the cells can mix within the channel 114 from the different areas in the canal thus resulting in the homogenized collection of cells from various areas of the vaginal canal. The homogenized cell sample will produce a more accurate examination of the cells, however the existing devices and methods allows to collect negative cells at one point in the canal while missing positive cells farther into the canal or the vice versa.

Figure 1:
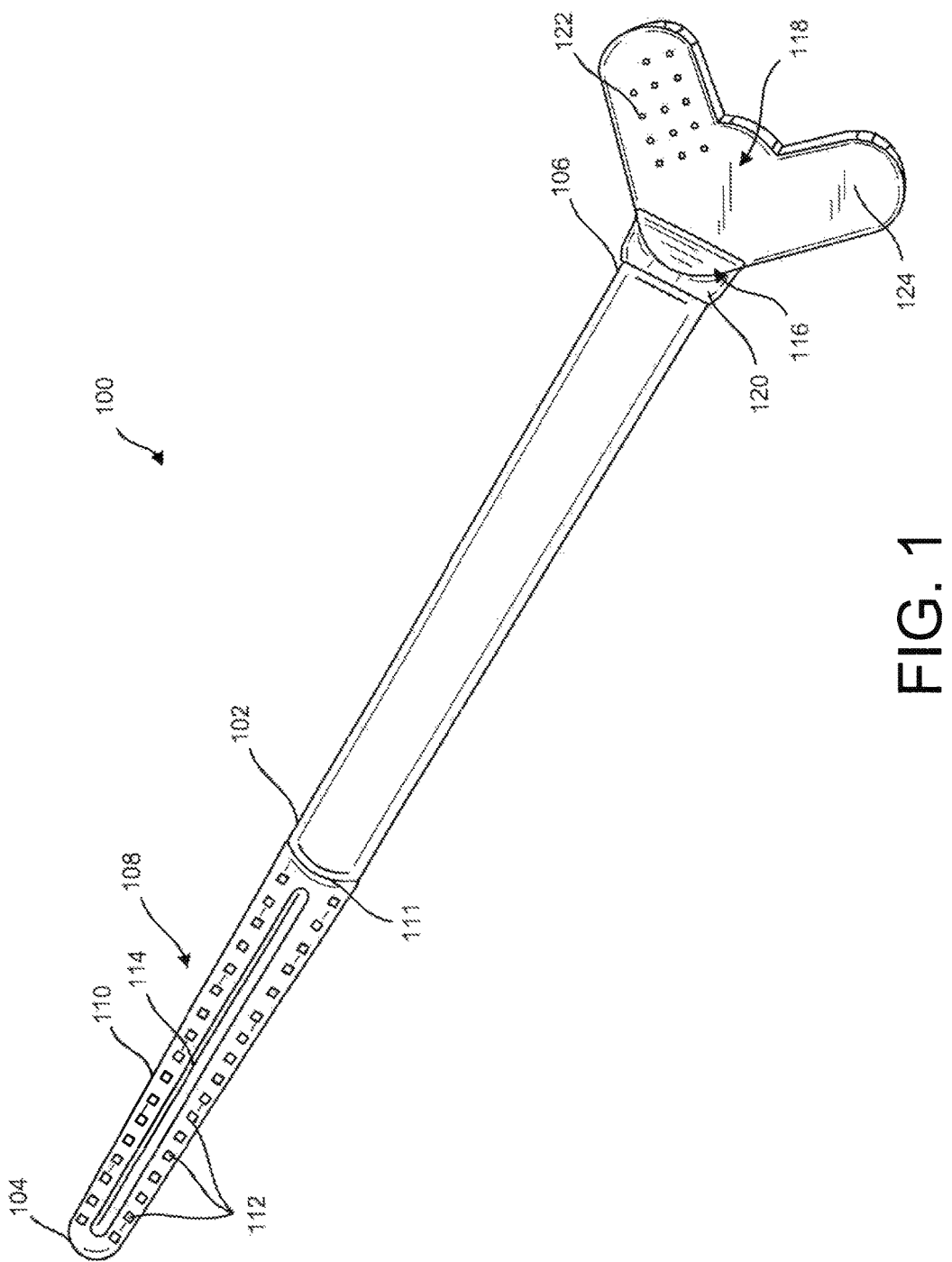
FIG. 1 illustrates a perspective view of an exemplary self-sampling device.

As referenced in FIG. 1, the device 100 for collecting vaginal cells or cervical cells by a user, wherein the device 100, comprising, a hollow, cylindrical elongated tubing 102 having a distal end 104 and a proximal end 106; a cell collecting area 108 disposed at the distal end 104 of the elongated tubing 104, wherein the cell collecting area 108 is covered by an adhesive collecting element 110 extending to a predetermined distance from the edge of the distal end 104. Further the collecting element 110 has plurality of ridges 112 to facilitate collection of cells; further the device 100 comprises a channel 114, wherein the channel 114 is disposed centrally within one side of the cell collecting area 108 elongating up to a predetermined distance from the edge of the distal end 104 of the tubing 102. The device 100 comprises a handle 116, wherein the handle 116 is disposed at the proximal end 106 of the tubing 102, further the handle 116 comprises an ergonomically shaped finger grip 118, wherein one end 122 of the finger grip 118 having a design or marking, the handle 116 and the tubing 102 is designed to form a unitary structure.

The device 100 of the present invention will greatly improve the ability of self-collect a good mix of different samples of viral charge of the cellular material from different areas of the female reproductive track. This invention in a difference of existing devices is comprised of a cell collecting area 108 covered by highly adhesive collecting element 110 that is 3.5 to 4.5 centimeters long and anywhere from 0.5 to 0.9 millimeters in diameter. The collecting area 108 is long enough to be in contact with different areas of the female reproductive track at all times while the self-sampling activity is taking place. In addition, the collecting element 110 is comprised of organized ridges 112 throughout the surface to improve cellular material retaining properties of the collecting element 110. The device 100 also comprises a channel 114 in one side of the cell collecting surface 108 which, goes from approximately 0.3 millimeters below the superior edge of the distal end 104 of the device 100 to approximately 0.3 millimeters before the bottom part 111 of the collecting element 110. This channel 114 will be approximately 0.3 millimeters in depth and 0.3 millimeters wide. The importance of the channel 114 is to improve the quantity of cells collected within one self-sampling exercise. The importance of having more cells collected is to perform different tests such as Polymerase Chain Reaction (PCR) to identify DNA of HPV and also to perform an Immunohistochemistry analysis to determine the progression of the viral infection to increase sensibility of the test results.

Those skilled in the art, in light of the present teachings, will recognize that different size and shape of the self-sampling device 100 and its elements can be used without any constraint to the type of material and without departing from the scope and spirit of the invention.

Figure 2:
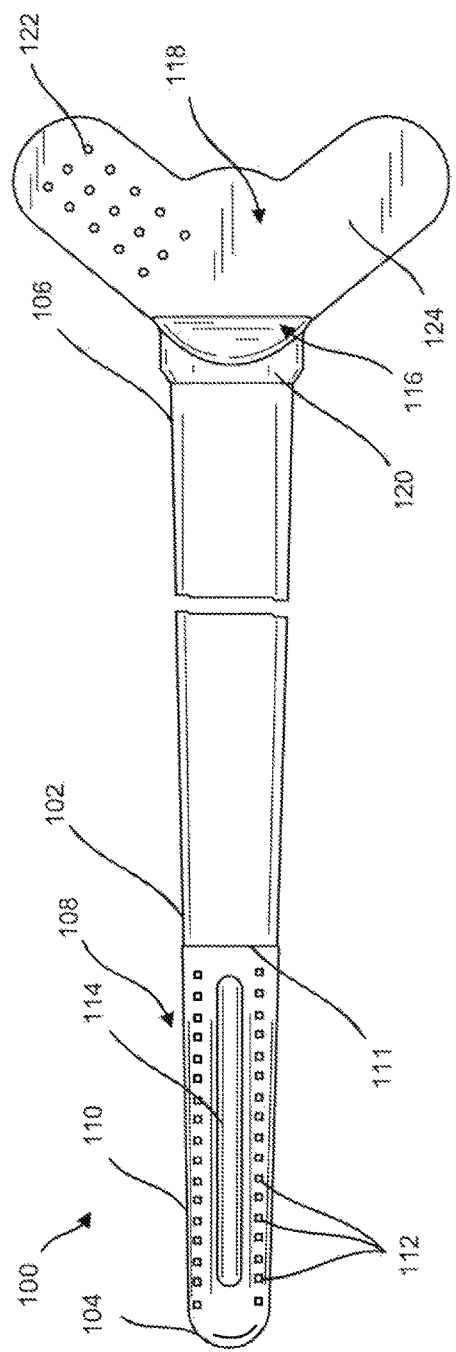
FIG. 2 illustrates a front view of the self-sampling device showing the front view of the channel.
Figure 3:
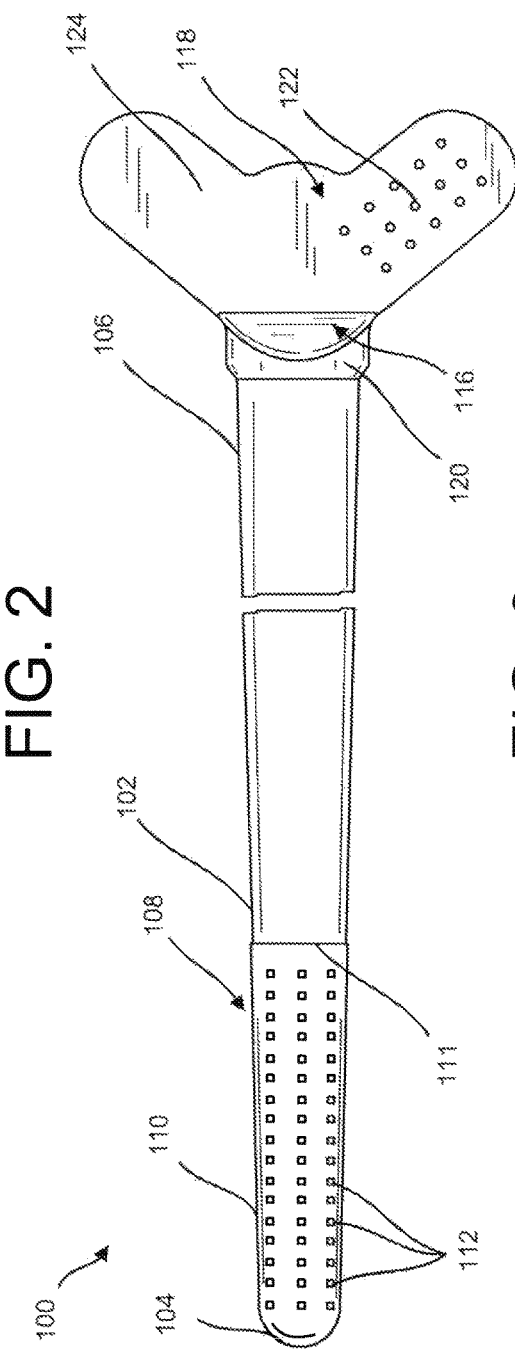
FIG. 3 illustrates a front view of the self-sampling device when rotated 180 degrees, thereby showing the side view of the channel.

As referenced in FIG. 2 and FIG. 3, in another embodiment of the present invention the device 100 comprises a finger grip 118 to allow a user to firmly hold the device with both the thumb and index fingers at the time of introducing the device 100 into her vaginal canal and then be able to easily clockwise rotate the device 100 three times before the device 100 is pulled from the vaginal canal. In addition, a texture in both sides of one end 122 of the finger grip 118 has been designed to facilitate the counting of 360 degrees rotations of the device 100 once inserted into the vaginal canal. Also, the ergonomically shaped finger grip 118 and the elongated tubing 102 is one piece to prevent that the device 100 can be introduced more than necessary to collect the cells. FIG. 2 illustrates a front view of the self-sampling device 100 showing the front view of the channel 114 while FIG. 3 illustrates a front view of the self-sampling device 100 when rotated 180 degrees, thereby showing the side view of the channel 114, such that when the textured design end 122 of the finger grip 118 reaches the position as shown in FIG. 2, the device 100 completes one complete 360 degrees rotation. Any such marking, design or visual difference of at least one side of one end 122 of the finger grip 118 facilitates the easy counting of 360 degrees rotations of the device 100.

Figure 4:
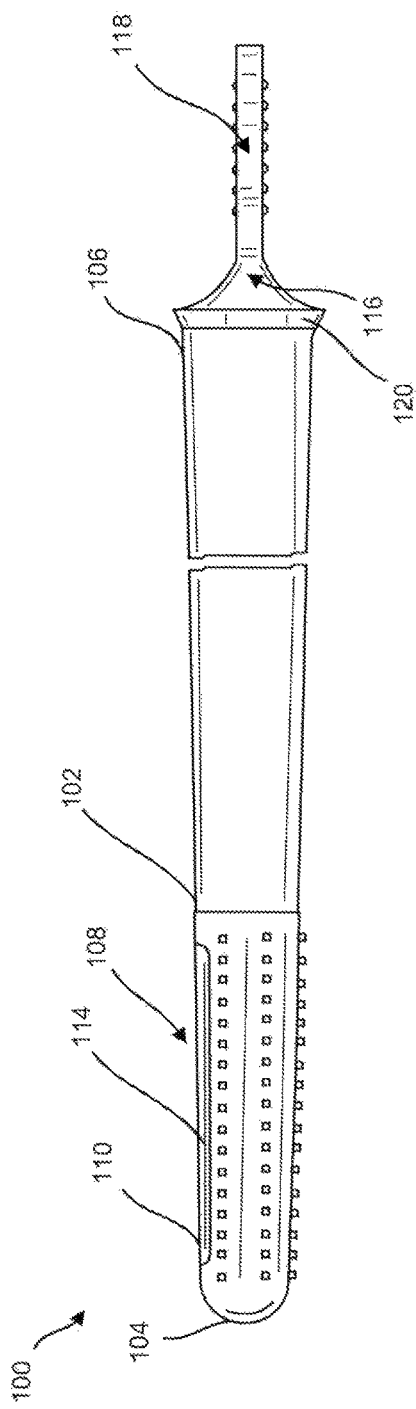
FIG. 4 illustrates a left side view of the self-sampling device.
Figure 5:
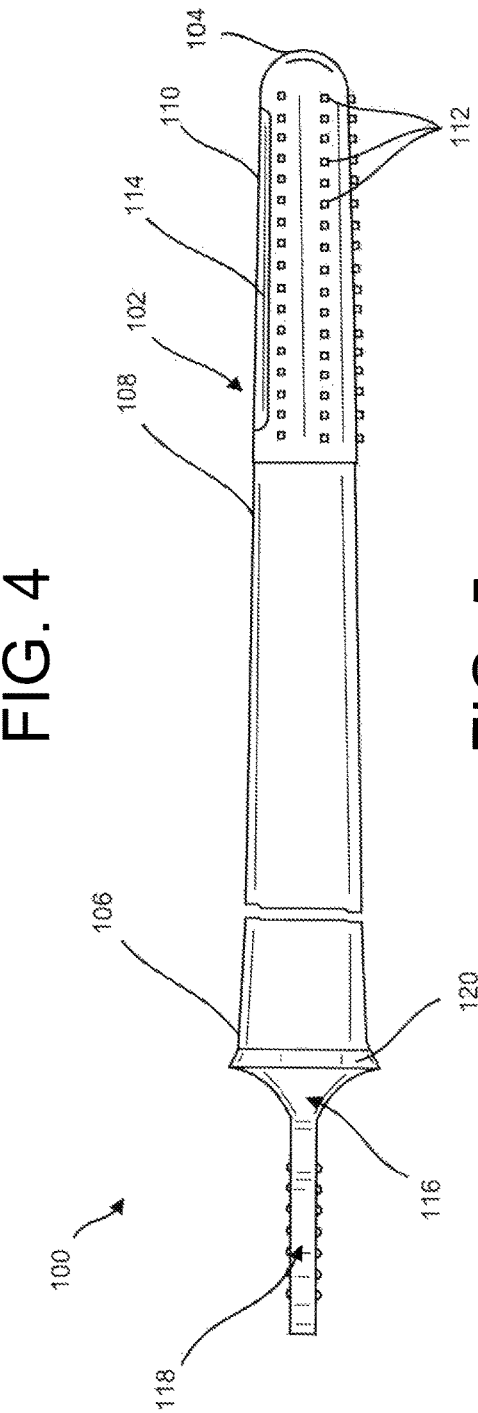
FIG. 5 illustrates a right side view of the self-sampling device.

FIG. 4 and FIG. 5 illustrating a left side view and a right side view respectively of the self-sampling device 100, showing the hollow, cylindrical elongated tubing 102, which is having a rounded tip, cylindrical body and slightly tapered configuration from its proximal end 106 to its distal end 104; the cell collecting area 108 disposed at the distal end 104, which is covered by an adhesive collecting element 110, further the collecting element 110 has plurality of organized ridges 112 and a channel 114 disposed along the length of the cell collecting area 108 for collecting the cells from different areas along length of the vaginal canal via one insertion of the device 100, so as to mix the cells within the channel 114 resulting in the homogenized collection of cells; and further a handle 116 attached to the base 120 of the device 100 and is disposed at the proximal end 106 of the tubing 102, wherein the handle 116 and the tubing 102 is designed to form a unitary structure.

Figure 6:
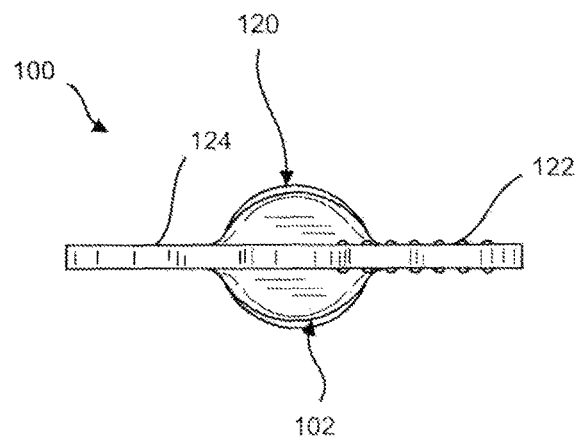
FIG. 6 illustrates a bottom view of the self-sampling device.
Figure 7:
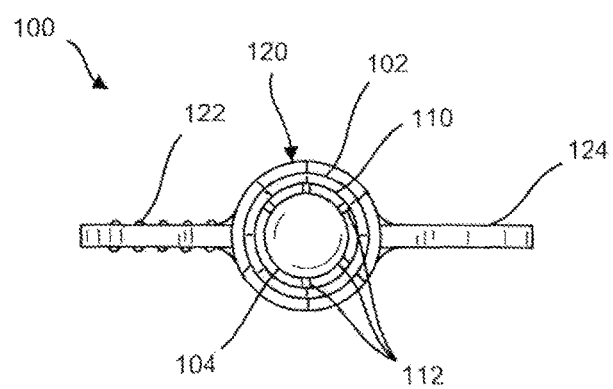
FIG. 7 illustrates a top view of the self-sampling device.

FIG. 6 and FIG. 7 illustrate a bottom view and a top view of the self-sampling device 100 respectively. The handle 116 is disposed at the proximal end 106 of the tubing 102 and is attached to the base 120 of the device 100, further the handle 116 comprises a butterfly shaped finger grip 118, wherein both sides of one end 122 of the finger grip 118 is texture designed to facilitate counting predetermined number of 360 degrees rotations of the device 100 once inserted into the vaginal canal, further the handle 116 and the tubing 102 is designed to form a unitary structure so as to prevent the device 100 to be introduced more than necessary to collect the cells.

In an exemplary embodiment of the invention as illustrated in FIG. 1-7 illustrating a method for collecting vaginal cells or cervical cells by a user, wherein the method, comprising the steps of, holding a handle 116 of a self-sampling device 100, wherein the device 100 comprising a hollow, cylindrical elongated tubing 102 having a distal end 104 and a proximal end 106, wherein the handle 100 is disposed at the proximal end 106 of the tubing 102 and is attached to the base 120 of the device 100 and a cell collecting area 108 disposed at the distal end 104 of the elongated tubing 102; inserting the device 100 into the vaginal canal; rotating the device 100 by the patient herself for at least three number of 360 degrees rotations to secure proper cell collection, wherein the handle 116 comprises a butterfly shaped finger grip 118 having both sides of one end 122 of the finger grip is texture designed and another end 124 is not textured or marked to facilitate counting predetermined number of 360 degrees rotations of the device 100, further the handle 116 and the tubing 102 is one piece to prevent the device 100 to be introduced more than necessary into the vaginal canal to collect the cells; and collecting the cells by a cell collecting area 108 having a channel 114 disposed along the length of the cell collecting area 108 for accumulating homogenized sample of cells from different areas within the vaginal canal via one insertion of the device 100.

In another embodiment of the invention, the cell collecting area 108 is covered by an adhesive collecting element 110 that is 3.5 to 4.5 centimeters long and 0.5 to 0.9 millimeters in diameter, wherein the adhesive collecting element 110 facilitate improved cellular material retaining properties of the device 100. However the collecting elements 110 having different adhesion techniques without restriction to its length and diameter can be used without departing from the scope and spirit of the invention.

In another embodiment of the invention, the channel 114 is disposed between two rows of the collection ridges 112 within one side of the cell collecting area 108 elongating from approximately 0.3 millimeters below the edge of the distal end 104 of the tubing 102 to approximately 0.3 millimeters before the bottom part 111 of the collecting element 110, wherein the channel 114 is 0.2 to 0.4 millimeters in depth and 0.2 to 0.4 millimeters wide. However more than one channel 114 without restriction to its size and shape can be disposed to improve more homogenized cell collection and accumulation within the channel 114 so as to conduct several tests using the enough cells collected by the single insertion of the device 100 in the vaginal canal of the user, further the channel 114 can be disposed throughout the length of the collecting area 108 or at a predetermined portion of the length of the collecting area 108 at a predetermined distance from the edge of the distal end 104 or proximal end 106 of the tubing 102 can be used without departing from the scope and spirit of the invention.

In some embodiments, the collecting element 110 has organized ridges 112 throughout the surface to improve cellular material retaining properties of the collecting element 110, wherein in an example of the device 100 shows the organized arrangement of the ridges 112 are in at least six parallel rows and at least seventeen ridges per row throughout length of the cell collecting area 108. However any number of ridges arranged in any suitable fashion keeping in mind maximum cell collection and user's comfort can be used without departing from the scope and spirit of the invention.

These and other scope and advantages of the invention will be further understood and appreciated by those skilled in the art by reference to the written specification, claims and appended drawings.

Because many modifications, variations, and changes in detail can be made to the described preferred embodiments of the invention, it is intended that all matters in the foregoing description and shown in the accompanying drawings be interpreted as illustrative and not in a limiting sense. Thus, the scope of the invention should be determined by the appended claims and their legal equivalence.

What is claimed is:

1. A device for collecting vaginal cells or cervical cells by a user, wherein the device, comprising:
    a hollow, cylindrical elongated tubing having a distal end and a proximal end;
    a cell collecting area disposed at the distal end of the elongated tubing, wherein the cell collecting area is covered by an adhesive collecting element that is approximately 3.5 to 4.5 centimeters long and approximately 0.5 to 0.9 millimeters in diameter extending to a predetermined distance from the edge of the distal end, further the collecting element has plurality of ridges;
    at least one channel, wherein the channel is disposed centrally within one side of the cell collecting area elongating up to a predetermined distance from the edge of the distal end of the tubing; and
    a handle, wherein the handle is disposed at the proximal end of the tubing, further the handle comprises an ergonomically shaped finger grip, wherein one end of the finger grip having a design or marking, the handle and the tubing is designed to form a unitary structure.

2. The device of claim 1, wherein the collecting area elongating from approximately 0.3 millimeters below the edge of the distal end of the tubing to approximately 0.3 millimeters before the bottom part of the collecting element.

3. The device of claim 1, wherein the channel is 0.3 millimeters in depth and 0.3 millimeters wide.

4. The device of claim 1, wherein the ergonomic shape of the finger grip of the handle is butterfly shaped.

5. The device of claim 1, wherein both sides of one end of the finger grip is texture designed or marked to facilitate counting predetermined number of 360 degrees rotations of the device once inserted into the vaginal canal.

6. The device of claim 1, wherein the ridges are arranged in organized fashion in at least six rows and at least seventeen ridges per row throughout the cell collecting area.

7. A self-sampling device for collecting vaginal cells or cervical cells by a user, wherein the device, comprising:
    a hollow, cylindrical elongated tubing having a distal end and a proximal end;
    a cell collecting area disposed at the distal end of the elongated tubing, wherein the cell collecting area is covered by an adhesive collecting element that is 3.5 to 4.5 centimeters long and 0.5 to 0.9 millimeters in diameter, further the collecting element has organized ridges throughout the surface of the cell collecting area to improve cellular material retaining properties of the collecting element;
    a channel, wherein the channel is disposed within one side of the cell collecting area elongating from approximately 0.3 millimeters below the edge of the distal end of the tubing to approximately 0.3 millimeters before the bottom part of the collecting element, wherein the channel is 0.2 to 0.4 millimeters in depth and 0.2 to 0.4 millimeters wide; and
    a handle, wherein the handle is disposed at the proximal end of the tubing and is attached to the base of the device, further the handle comprises a butterfly shaped finger grip, wherein both sides of one end of the finger grip is texture designed to facilitate counting predetermined number of 360 degrees rotations of the device once inserted into the vaginal canal, further the handle and the tubing is designed to form a unitary structure.

8. The device of claim 7, wherein the organized arrangement of the ridges are in at least six rows and at least seventeen ridges per row throughout the cell collecting area.

9. A device for collecting a homogenized sample of cells from different areas within the vaginal canal by a user, wherein the device, comprises:
    a hollow, cylindrical elongated tubing having a distal end and a proximal end;
    a cell collecting area disposed at the distal end of the elongated tubing, wherein the cell collecting area is covered by an adhesive collecting element that is approximately 3.5 to 4.5 centimeters long and approximately 0.5 to 0.9 millimeters in diameter extending to a predetermined distance from the edge of the distal end, further the collecting element has plurality of organized ridges arranged in several parallel rows along the length of the cell collecting area;
    channel, wherein the channel is disposed along the length of the cell collecting area for collecting the cells from different areas along length of the vaginal canal via one insertion, so as to mix the cells within the channel resulting in the homogenized collection of cells; and
    a handle, wherein the handle is disposed at the proximal end of the tubing, further the handle comprises an ergonomically shaped finger grip, wherein one end of the finger grip has a design or marking, the handle and the tubing is designed to form a unitary structure.

10. The device of claim 9, wherein the collecting area elongating from approximately 0.3 millimeters below the edge of the distal end of the tubing to approximately 0.3 millimeters before the bottom part of the collecting element.

11. The device of claim 9, wherein the channel is 0.3 millimeters in depth and 0.3 millimeters wide and the channel is disposed between two rows of collection ridges.

12. The device of claim 9, wherein the ergonomic shape of the finger grip of the handle is butterfly shaped.

13. The device of claim 9, wherein both sides of one end of the finger grip is texture designed or marked to facilitate counting predetermined number of 360 degrees rotations of the device once inserted into the vaginal canal.

14. The device of claim 9, wherein the ridges are arranged in organized fashion in at least six parallel rows and at least seventeen equidistant ridges per row throughout the cell collecting area.

* * * * *